United States Patent [19]

Goins et al.

[11] Patent Number: 4,560,809

[45] Date of Patent: Dec. 24, 1985

[54] ALKYLATION PROCESS

[75] Inventors: Dixie E. Goins; Harold V. Huggins; Edward A. Burt, all of Orangeburg; Silas W. Holmes, Columbia, all of S.C.

[73] Assignee: Ethyl Corporation, Richmond, Va.

[21] Appl. No.: 658,523

[22] Filed: Oct. 9, 1984

[51] Int. Cl.$^4$ .................... C07C 37/11; C07C 38/06
[52] U.S. Cl. .................... 568/789; 568/784; 568/785; 568/794
[58] Field of Search ............. 568/784, 789, 785, 794

[56] References Cited

U.S. PATENT DOCUMENTS

| | | | |
|---|---|---|---|
| 2,831,898 | 4/1958 | Ecke et al. | 568/789 |
| 3,200,157 | 8/1965 | Buls et al. | 568/789 |
| 3,355,504 | 11/1967 | Coffield et al. | 568/794 |
| 3,367,981 | 2/1968 | Napolitano | 568/789 |
| 3,426,082 | 2/1969 | Curry et al. | 568/789 |
| 3,461,175 | 8/1969 | Kulik et al. | 568/785 |
| 3,652,685 | 3/1972 | Geddes | 568/789 |

FOREIGN PATENT DOCUMENTS

| | | | |
|---|---|---|---|
| 672377 | 10/1963 | Canada | 568/789 |
| 708203 | 4/1965 | Canada | 568/789 |
| 1809555 | 10/1969 | Fed. Rep. of Germany | 568/789 |
| 1062298 | 2/1967 | United Kingdom | 568/789 |
| 1229480 | 4/1971 | United Kingdom | 568/789 |

*Primary Examiner*—Werren B. Lone
*Attorney, Agent, or Firm*—Donald L. Johnson; John F. Sieberth; John F. Hunt

[57] ABSTRACT

A process for the production of a 2,6-dialkylphenol in high yield wherein the alkyl groups are secondary or tertiary with a reduced overall production of 4-alkylphenol by-products by the aluminum phenoxide catalyzed pressure reaction of isobutylene with phenol and a mixture of 2,4-dialkylphenol and 2,4,6-trialkylphenol which may be obtained, in a cyclic process, as a bottom stream from the distillation of the reaction mixture to obtain the 2,6-dialkylphenol product.

19 Claims, No Drawings

ALKYLATION PROCESS

BACKGROUND OF THE INVENTION

The present invention relates in general to alkylated phenols and specifically to catalyzed pressure reactions of olefins with phenols to produce alkylated phenols.

Alkylated phenols are widely used as antioxidants for various substrates, as building blocks for polymers, as intermediates for the production of a wide variety of products, and for other specific end uses. Of particular importance are the mono- and di- orthoalkylated phenols. The compound 2,6-di-tert-butylphenol, for example, has been widely used for the production of various diphenols and for the well-known 4,4'-methylenebis(2,6-di-tert-butylphenol)antioxidant.

The compound 2,6-di-tert-butylphenol and various 2,6-di-alkylphenols may be synthesized by various catalytic routes including the pressure reaction of an olefin with phenol in the presence of a catalyst. Such processes typically produce a substantial portion of para-alkylated phenols which have only limited applications and are generally available in great quantity but must nevertheless be burned to obtain merely their fuel value. As used herein the term "para-alkylphenol" means any phenol having at least a para-alkyl substituent. These para-alkylphenols include para-tert-butylphenol, para-isopropylphenol, 2,4-di-sec-butylphenol, 2,4-di-tert-butylphenol, 2,4-diisopropylphenol, 2-isopropyl-4-tert-butylphenol, 2,4,6-triisopropylphenol, 2,4,6-tri-tert-butylphenol, 2,4,6-tri-sec-butylphenol, and various other compounds.

The aluminum phenoxide catalyzed reaction of an olefin gas with phenol is carried out by heating about 100 parts by weight phenol with about 1 part fresh aluminum metal at about 150° C. to form an aluminum phenoxide catalyst and thereafter reacting the phenol containing the catalyst with a $C_3$ or higher olefin usually at high pressure up to about 1,000 psig, for anywhere from about 15 minutes to a few hours so as to alkylate the phenol to form the desired product 2,6-dialkylphenol wherein the alkyl groups are secondary or tertiary. The catalyst in the resultant reaction mixture is killed and the reaction mixture is typically distilled to remove light ends including unreacted phenol and, subsequently, 2,6-dialkylphenol product, leaving 2,4-dialkylphenol and 2,4,6-trialkylphenol in the bottoms.

Typically, the light ends from the first distillation of the resultant reaction mixture contain some ortho-tert-butylphenol and some para-tert-butylphenol as well as, mainly, unreacted phenol. Any olefin gas coming overhead is recovered by a venting process and condensed for reuse. The overhead light ends may be recycled for reaction in the aluminum phenoxide catalyzed pressure reaction to make additional 2,6-dialkylphenol.

The subsequent distillation after removal of the light ends typically permits recovery of the product 2,6-dialkylphenol from the top of a second column and generates a column bottom stream containing the isomer 2,4-dialkylphenol and the homolog 2,4,6-trialkylphenol as well as a portion of product 2,6-dialkylphenol. Typically, the column bottoms also contain small portions of materials which appear to be biphenols, higher alkyl-substituted phenols (higher than expected from the olefin used), and some meta-substituted phenols.

The typical aluminum phenoxide catalyzed reaction described above results in the production of about 10–12 weight percent based upon the amount of phenol of para-alkylated phenols i.e., alkylphenols having substituents in the 4- position, especially 2,4-dialkylphenol and 2,4,6-trialkylphenol. Such a stream is often subjected to a dealkylation reactor in an attempt to recover additional phenol and olefin or used as a fuel source to at least recover its heat value.

SUMMARY OF THE INVENTION

The present invention is a process for the production of a high yield of 2,6-dialkylphenols wherein the alkyl groups are secondary or tertiary with the limited production of para-alkylphenols i.e., 4-alkylphenols.

We have discovered that the substitution of the column bottoms material described above or an equivalent mixture containing 2,4-dialkylphenol and 2,4,6-trialkylphenol for up to about 30 parts by weight of the phenol reactant in the aluminum phenoxide catalyzed reaction described above does not provide a cumulative effect in the production of by-product para-alkylated phenols. That is, one would expect that, for example, the reaction of 80 parts by weight phenol and 20 parts by weight column bottoms mixture containing 2,4-dialkylphenol and 2,4,6-trialkylphenol would result in the production of 80% of the expected para-alkylphenols or about 8–10% of para-alkylphenols plus the accumulation of the para-alkylphenols which were supplied from the 2,000 pounds of mixture i.e., an additional 10–12% para-alkylated phenols. It would be expected then that such a reaction would produce about 18–19% by weight of the para-alkylated phenolic materials. However, and quite unexpectedly, the process of the invention provides a reaction mixture which contains only about 14% of the para-alkylphenols. Thus, on a cyclic basis, we have found that the overall production of the less desirable para-alkylphenol by-products may be cut by as much as 30% and possibly more than 50% with the concurrent increase in the production of the desirable product 2,6-dialkylphenol.

The present invention is a process for the production of 2,6-dialkylphenols wherein the alkyl groups are secondary or tertiary, said process comprising the steps of: (a) reacting a $C_3$ or higher olefin and a phenolic mixture comprising at least about 70 weight percent phenol optionally containing 2-alkylphenol and up to about 30 weight percent of a para-alkylphenol mixture comprising mainly 2,4-dialkylphenol and 2,4,6-trialkylphenol wherein the alkyl groups are secondary or tertiary, in the presence of an aluminum phenoxide catalyst to form an alkylation mixture and (b) recovering 2,6-dialkylphenol from said alkylation mixture.

The present invention is also a cyclic process for the production of 2,6-dialkylphenol wherein said alkyl groups are secondary or tertiary with reduced overall production of para-alkylphenols, comprising: (a) reacting a phenol mixture with a $C_3$ or higher olefin in the presence of an aluminum phenoxide catalyst, said phenol mixture comprising mainly phenol and optionally ortho-alkylphenol and being further characterized by containing up to about 30 weight percent of a mixture comprising 2,4-dialkylphenol and 2,4,6-trialkylphenol wherein the alkyl groups are secondary or tertiary; (b) distilling the 2,6-dialkylphenol product leaving distillation bottoms comprising mainly 2,4-dialkylphenol, and 2,4,6-trialkylphenol; (c) recycling at least part of said bottoms to a subsequent aluminum-phenoxide catalyzed reaction with phenol and a $C_3$ or higher olefin and (d) repeating steps (a), (b), and (c) so as to achieve an overall higher yield of 2,6-dialkylphenol.

The present invention is also a cyclic process for the production of 2,6-dialkylphenols wherein alkyl groups are sec- or tert- alkyl groups, said process comprising (a) reacting a phenolic reactant comprising mainly phenol optionally containing a 2-alkylphenol and optionally containing a para-alkylphenol mixture with a $C_3$ or higher olefin in the presence of an aluminum phenoxide-type catalyst to form an alkylation mixture (b) distilling said 2,6-dialkylphenol from said alkylation mixture leaving distillation bottoms comprising a para-alkylphenol mixture comprising 2,4-dialkylphenols and 2,4,6-trialkylphenols and (c) recycling at least part of said bottoms to a subsequent cyclic process conducted in the same manner including the above steps (a) and (b) wherein, in said subsequent cyclic process said bottoms form up to about 30 weight percent of said phenolic reactant.

DESCRIPTION OF THE PREFERRED EMBODIMENT

A preferred embodiment of the present invention is a process for the production of 2,6-dialkylphenols wherein the alkyl groups are secondary or tertiary, said process comprising the steps of: (a) reacting a $C_3$ or higher olefin and a phenolic mixture comprising at least about 70 weight percent phenol optionally containing 2-alkylphenol and up to about 30 weight percent of a para-alkylphenol mixture comprising mainly 2,4-dialkylphenol and 2,4,6-trialkylphenol wherein the alkyl groups are secondary or tertiary, in the presence of an aluminum phenoxide catalyst to form an alkylation mixture and (b) recovering 2,6-dialkylphenol from said alkylation mixture. According to the preferred embodiment, the reaction is carried out in the presence of an aluminum phenoxide type catalyst so as to recover a high yield of 2,6-dialkylphenol wherein the alkyl groups are secondary or tertiary.

The catalysts of the invention are of the aluminum phenoxide type. By "aluminum phenoxide" type is meant those catalysts formed by reaction of aluminum or an aluminum compound with a phenolic compound to form at least one bond from the aluminum atom to the oxygen atom of the phenol. Typical of these types of catalyst is the aluminum triphenoxide species which has been shown to exist in various reaction systems. Likewise phenoxy aluminum halides are useful as aluminum phenoxide type catalysts. These include diphenoxy aluminum chloride, phenoxy aluminum dichloride, diphenoxy aluminum bromide and the like. These are readily made by reacting a phenol with an aluminum trihalide such as $AlCl_3$ and venting a portion of the hydrogen halide evolved preferably with the assistance of an inert gas (e.g., $N_2$) purge. Alternatively they may be made by reaction of a phenol with an alkyl aluminum halide such as dialkyl aluminum chloride, alkyl aluminum dichloride, methylaluminum sesquichloride, dialkyl aluminum bromide and the like.

The phenoxy aluminum hydroxides have also been used as aluminum phenoxide type catalysts in this alkylation reaction. These are easily formed by including a very small amount of water in the phenol from which the aluminum phenoxide type catalyst is made. Any of these types of aluminum phenoxide catalysts are suitable for the invention to bring about a high yield of 2,6-dialkylphenol according to the described process.

U.S. Pat. No. 2,831,898 discloses a process for selectively introducing hydrocarbon groups onto the nuclear ring of a phenol compound using as a catalyst an aluminum phenoxide material. That patent is incorporated herein by reference in its entirety. Also of pertinence to the present invention for their disclosure with regard to catalyst materials and recovery of the product and separation of the catalyst materials after reaction are U.S. Pat. Nos. 3,652,685; 3,426,082; and 3,367,981 which are also incorporated herein by reference in their entirety. These patents describe some of the aluminum phenoxide type catalyst materials of the invention and their pertinence to orthoalkylation of phenolic materials.

The main reaction ingredient of the process of the invention is phenol. The phenol reactant may optionally include some ortho-sec-alkylphenol or ortho-tert-alkylphenol which is also alkylated according to the process of the invention to form the desired product 2,6-dialkylphenol wherein the alkyl groups are secondary or tertiary. Thus suitable starting materials include not only the compound phenol but also ortho-tert-butylphenol, ortho-isopropylphenol, ortho-sec-butylphenol, ortho-tert-amylphenol, and the like.

The various alkyl substituents of the invention are those secondary or tertiary alkyl groups having from 3 up to about 20 carbon atoms.

The main products of the invention are the 2,6-dialkylphenols wherein the alkyl groups are secondary or tertiary. Exemplary compounds of the invention include: 2,6-di-tert-butylphenol; 2,6-di-tert-amylphenol; 2,6-diisopropylphenol; 2,6-di-sec-butylphenol; 2-isopropyl-6-tert-butylphenol; 2-sec-butyl-6-tert-butylphenol; and the like. A more preferred class of products according to the invention are the 2,6-di-tert-alkylphenols since these compounds are found to be prepared in very high yields according to the process of the invention whereas the 2,6-di-secondary-alkylphenols may also be readily prepared by various other catalyst systems and reaction processes. Still more preferred are the 2,6-di-tert-alkylphenols where the alkyl groups are identical. The most preferred product of the invention is 2,6-di-tert-butylphenol.

The reaction by-products comprise a mixture which contains a significant portion of 2,4-dialkylphenol and 2,4,6-trialkylphenol. These compounds typically have all of the alkyl substituents identical although it is not unusual for isomeric forms of such compounds to be present. For example, where all of the alkyl substituents are butyl, it is not unusual for some of the substituents to be n-butyl or sec-butyl where the tert-butyl substituent predominates. A preferred by-product suitable for recycle according to the present invention comprises a mixture of a 2,4-dialkylphenol and 2,4,6-trialkylphenol wherein the alkyl groups are secondary or tertiary and the mixture additionally contains minor portions of other components typically found as by-products in the alkylation of phenols. Such by-products include phenols having 2,4-, 2,4,6-, or even 2,6- alkylation wherein the alkyl groups may or may not be tertiary or secondary and in fact are often larger alkyl groups. For example, in the alkylation of a phenol with isobutylene, at least one component is frequently identified as having octyl substituents. Some meta-substituted phenols may also be present in aluminum phenoxide catalyzed reactions of phenols.

According to the process of the invention, the combination of phenol (optionally with or without some additional components such as ortho-alkylphenol) and a mixture of 2,4-dialkylphenol and 2,4,6-trialkylphenol (optionally with additional alkylated phenolic components) is pressure reacted with a $C_3$ or higher olefin such as isopropylene, isobutylene, or the like in the presence of an aluminum phenoxide catalyst to form a reaction mixture.

The alkylation is conducted at pressures from about 100 psig up to 1,000 psig or higher. The reaction temperature should be high enough to cause the reaction to proceed but not so high as to cause extensive decomposition. A useful temperature range is about 75°–250° C., more preferably about 100°–175° C. Following the alkylation the aluminum phenoxide type catalyst is usually deactivated or "killed" to prevent dealkylation during distillation. This can be accomplished by adding water preferably containing sufficient acid (e.g. acetic acid, HCl, etc.) to prevent formation of alumina gel. The water phase containing aluminum residue is separated prior to distillation.

The 2,6-dialkylphenol product may be recovered by any of various means but distillation is commonly used. For example, the reaction mixture may be directed to two distillation columns in series. In the first distillation, the reaction mixture is distilled so as to remove light ends such as the mono-alkylated phenols such as ortho-tert-butylphenol, ortho-isopropylphenol, and unreacted phenol along with any unreacted isobutylene which may be vented and recovered by condensation. The ortho-alkylphenols can be recycled with the phenol charged to a subsequent alkylation. The remainder of the reaction mixture coming off the bottom of the first column contains the desired product 2,6-dialkylphenol such as 2,6-di-tert-butylphenol or 2,6-diisopropylphenol. This remainder of the reaction product is then directed to a second column which is operated so as to remove the desired product 2,6-dialkylphenol overhead and withdraw a bottom stream containing some of the desired product but also including all of the higher boiling components used for recycle. For example, in the operation of an alkylation process for the production of 2,6-di-tert-butylphenol by the pressure reaction of isobutylene with phenol and a mixture of 2,4-di-tert-butylphenol and 2,4,6-tri-tert-butylphenol according to the process of the invention a typical column bottoms product from the second distillation column includes:

| Compound | % |
| --- | --- |
| 2,6-di-tert-butylphenol (desired product) | 7.4 |
| 2,4-di-tert-butylphenol | 6.6 |
| 2,5-di-tert-butylphenol (or octylphenol ?) | 5.9 |
| 2,4,6-tri-tert-butylphenol | 63.2 |
| dioctylphenol | 1.3 |
| 4,4'-bis(2,6-di-tert-butylphenol) | 6.5 |
| Heavy Ends | 9.1 |

As can readily be seen from the above described description of the bottoms from the second column the primary components are 2,4,6-trialkylphenol and 2,4-dialkylphenol. A more preferred embodiment of the invention comprises the use of a homogeneous portion of the reaction column bottoms described above for about 30 weight percent of the initial phenolic reactants. Of course various other streams or compositions containing primarily 2,4-dialkylphenol and 2,4,6-trialkylphenol wherein the alkyl substituents are secondary or tertiary may also be used according to the process of the invention.

According to the process of the invention, the phenolic component having an open ortho position for alkylation is predominantly phenol but may contain up to about 30 parts by weight of a mixture 2,4-dialkylphenol and 2,4,6-trialkylphenol. More preferably, the phenolic component is at least about 80 parts by weight phenol. We have found that by replacing about 20% by weight of the starting phenol for alkylation with the heavy components from distillation of the desired reaction product 2,6-dialkylphenol that the overall yield on starting material is improved and the heavy by-products are reduced by about 50%. According to a preferred embodiment of the invention, the aluminum phenoxide catalyst is first formed by reaction of aluminum with phenol and then the additional portion of the mixture of 2,4-dialkylphenol and 2,4,6-trialkylphenol is added for the pressure reaction with a $C_3$ or higher olefin, preferably isobutylene.

The remainder of the heavier materials from the column bottoms from recovery of the desired reaction product 2,6-dialkylphenol may be used for their heat value or directed to a dealkylation reactor which may also use an aluminum phenoxide type catalyst at high temperature to dealkylate the para position of the phenolic components to provide starting material phenol or orthoalkylphenol such as ortho-tert-butylphenol.

The process of the invention is suitably carried out by first forming an aluminum phenoxide catalyst by the reaction of about 1 part by weight aluminum with about 80–100 parts by weight of phenol at about 150°–200° C. to form an aluminum phenoxide catalyst. After the catalyst formation and venting of the formed hydrogen gas, the reaction is carried out by, preferably, adding the mixture of 2,4-dialkylphenol and 2,4,6-trialkylphenol wherein the alkyl groups are secondary or tertiary and heating to about 100° C. while pressurizing with isobutylene feed over a period of about 1 hour. A typical reaction pressure reaches a maximum of about 400 psig but may be permitted to go much higher.

A suitable range of temperature for preparation of the catalyst is about 75° to about 250° C. A suitable range of reaction temperature is about 75° to 150° C. Reaction pressures may vary from about 100 to 1,000 psig.

A better understanding of the invention will be had by a review of the following examples.

EXAMPLE I

To a reactor were charged 80 parts by weight of phenol and 1 part by weight of comminuted pure aluminum. The reaction vessel was sealed and heated to about 150° C. and held at that temperature for about 5 minutes to form the aluminum phenoxide catalyst. Thereafter, the vessel was vented and cooled to ambient temperature. Thereafter, 17 parts by weight of a column bottom stream comprising about 40 weight percent 2,4,6-tri-tert-butylphenol, about 20 weight percent 2,4-di-tert-butylphenol, about 15 weight percent 2,6-di-tert-butylphenol, and about 15 weight percent of other alkylated phenols was added. The reaction vessel was sealed and heated to about 100° C. Isobutylene was fed under pressure into the reactor over a period of about 20 minutes and at a reaction pressure of about 200 psig. Thereafter, the reaction was allowed to continue for another hour whereupon uptake of isobutylene ceased. The reaction vessel was cooled and vented to provide an excellent yield of the desired product 2,6-di-tertbutylphenol. Thereafter, the catalyst of the reaction mixture was killed with aqueous sulfuric acid containing about 1.0% nitric acid (to inhibit corrosion of the stainless steel wash kettle) in a known manner and the reaction mixture was distilled to remove light ends which comprise mostly phenol and some ortho-tert-butylphenol. The bottom stream from the first column was distilled in a second column which permitted recovery of 2,6-di-tert-butylphenol overhead and gave a by-product bottom stream comprising primarily 2,4,6-tri-tert-butylphenol and 2,4-di-tert-butylphenol. A homogeneous portion of about half of the bottom stream from the second column along with the light ends of the first column was used in subsequent alkylations of phenol with isobutylene as described above.

Four runs according to the process of the invention were carried out as set forth above and the beginning and final reaction mixtures were analyzed. Table I below summarizes the analysis of the four runs giving the relative proportion of para-alkylphenols as the "mole % - para-alkylphenol" and listing the amount of isobutylene which was reacted per mole of aromatic ring including all of the components in the starting reaction mixture. Also listed is the ratio of new 2,6-di-tert-butylphenol product formed to new para-alkylphenol formed.

As can be seen from the table below, essentially all of the phenol component of the starting reaction mixture is reacted and an excellent yield of the desired 2,6-di-tert-butylphenol product is obtained. Also significant is the reduction of the amount of 2,4-di-tert-butylphenol isomer in each of the four runs. Notably, there was little increase in the amount of 2,4,6-tri-tert-butylphenol and the amount of 4-tert-butylphenol was decreased slightly.

TABLE I

| | | Run 1 | Run 2 | Run 3 | Run 4 | Comparative Run 5 |
|---|---|---|---|---|---|---|
| Mole % | (Start) | 12.20 | 10.77 | 10.47 | 12.92 | 4.50 |
| Para-alkylphenol | (End) | 18.42 | 19.12 | 13.20 | 17.23 | 12.63 |
| New 2,6-*/ New Para-alkylphenols | | 11.18 | 7.81 | 17.48 | 14.90 | 8.57 |
| Moles Isobutylene Reacted per Ring | | 2.070 | 2.019 | 1.731 | 1.99 | 1.93 |

ANALYSIS OF REACTION MIXTURE
Isobutylene Free Basis:

| COMPONENT | | COMPOSITION (WT. %) | | | | |
|---|---|---|---|---|---|---|
| Phenol | (Start) | 46.07 | 50.90 | 49.90 | 46.39 | 66.20 |
| | (End) | .67 | 1.14 | 1.56 | 0.68 | 1.40 |
| *OTBP | (Start) | 25.05 | 22.44 | 24.44 | 23.35 | 24.00 |
| | (End) | 4.52 | 6.65 | 24.79 | 9.41 | 8.50 |
| *PTBP | (Start) | 1.05 | .886 | 1.054 | 1.63 | 5.40 |
| | (End) | .073 | .257 | .118 | .23 | 0.40 |
| *2,6- | (Start) | 3.28 | 3.10 | 3.08 | 3.31 | 2.70 |
| | (End) | 70.11 | 66.14 | 53.03 | 66.15 | 72.40 |
| *2,4- | (Start) | 3.50 | 2.61 | 2.53 | 2.71 | 0.90 |
| | (End) | 1.82 | 2.09 | 1.75 | 1.75 | 1.70 |
| *2,4,6- | (Start) | 18.53 | 17.71 | 16.86 | 19.89 | 0.30 |
| | (End) | 20.48 | 20.85 | 15.54 | 19.22 | 13.50 |

*OTBP is ortho-tert-butylphenol; PTBP is 4-tert-butylphenol; 2,6- is 2,6-di-tert-butylphenol; 2,4- is 2,4-di-tert-butylphenol; and 2,4,6- is 2,4,6-tri-tert-butylphenol.

Also shown in Table I is a Comparison Run 5 representing the aluminum phenoxide catalyzed alkylation of phenol containing some ortho-tert-butylphenol with isobutylene in the same reactor and under the same conditions as Runs 1–4 but without recycled column bottoms (para-alkylphenols). A small amount of para-alkyl phenol (mostly 4-tert-butylphenol) is present from the recycle of the ortho-tert-butylphenol recovered overhead from the first of the two distillation columns. The production ratio of product to para-alkylphenols (New 2,6-/New para-alkylphenols) is clearly inferior for Run 5. Thus the overall production of para-alkylphenols is greater without recycle.

While the value is lower for Run 2, this occurred because the reaction was allowed to proceed beyond an optimun point resulting in the continued alkylation of 2,6-di-tert-butylphenol to 2,4,6-tri-tert-butylphenol. The value of 7.81 New 2,6-*/New Para-alkylphenols was determined from a sample taken after the optimum reaction point. Experience has now shown us that the optimum reaction point is usually after 1.7 but before 1.9 moles of butyl radical per aromatic ring are present on alkylated phenolic components (referred to as Moles of Isobutylene Reacted per Ring). Thus while Comparison Run 5 was stopped at an optimum point for 2,6-di-tert-butylphenol production, Run 2 was not.

We have also observed that runs in the same reactor on the same scale, and at the same temperature but with fresh phenol only (no ortho-tert-butylphenol or overhead) from the distillation column result in a New 2,6-*/New Para-tert-butylphenol ratio of about 4.5 to 7.0 at the optimum point.

The above described process of the present invention has resulted in a significant economic advantage in the production of 2,6-di-tert-butylphenol and corresponding advantages may be obtained for the production of other 2,6-dialkylphenols wherein the alkyl groups are secondary or tertiary.

While a preferred embodiment of the invention has been described above, certain parameters of the invention may be varied without departing from the scope or spirit of the invention as defined by the appended claims.

We claim:

1. A process for the production of 2,6-di-alkylphenols wherein the alkyl groups are secondary or tertiary, said process comprising the steps of: (a) reacting at about 100–1000 psig and 75°–250° C. a $C_3$–$C_{20}$ olefin and a phenolic mixture comprising at least about 70 weight percent phenol and about 20–30 weight percent of a para-alkylphenol mixture comprising mainly 2,4-dialkylphenol and 2,4,6-trialkylphenol wherein the alkyl groups are secondary or tertiary, in the presence of an aluminum phenoxide catalyst to form an alkylation mixture and (b) recovering 2,6-dialkylphenol from said alkylation mixture.

2. The process of claim 1 wherein said para-alkylphenol mixture is present in no more than about 20 weight percent.

3. The process of claim 1 wherein all of said alkyl groups are tertiary.

4. The process of claim 3 wherein said tertiary alkyl groups are tertiary butyl.

5. The process of claim 1 wherein said olefin is isobutylene and said 2,6-dialkylphenol is 2,6-di-tert-butylphenol.

6. The process of claim 1 wherein said para-alkylphenol mixture comprising mainly 2,4-di-alkylphenol and 2,4,6-trialkylphenol also contains a phenol with an octyl substituent.

7. The process of claim 1 wherein said para-alkylphenol mixture comprises the bottoms from the distillation of 2,6-dialkylphenol from an alkylation mixture formed by the aluminum phenoxide catalyzed reaction of a $C_3$–$C_{20}$ olefin with phenol wherein said alkyl groups are secondary or tertiary.

8. The process of claim 7 wherein said alkyl groups of the reaction product are tertiary.

9. The process of claim 8 wherein the tertiary alkyl groups of the reaction product are tert-butyl.

10. The process of claim 7 wherein said $C_3$–$C_{20}$ olefin is isobutylene.

11. The process of claim 1 wherein said aluminum phenoxide catalyst is formed by reacting aluminum metal with said phenol.

12. A cyclic process for the production of 2,6-dialkylphenol wherein said alkyl groups are secondary or tertiary with reduced overall production of para-alkylphenols, comprising: (a) reacting at about 100–1000 psig and 75°–250° C. a phenol mixture with a $C_3$–$C_{20}$ olefin in the presence of an aluminum phenoxide catalyst, said phenol mixture comprising mainly phenol and being further characterized by containing about 20–30 weight percent of a mixture comprising 2,4-dialkylphenol and 2,4,6-trialkylphenol wherein the alkyl groups are secondary or tertiary; (b) distilling the 2,6-dialkylphenol product leaving distillation bottoms comprising mainly 2,4-dialkylphenol, and 2,4,6-trialkylphenol; (c) recycling at least part of said bottoms to a subsequent aluminum phenoxide-catalyzed reaction with phenol and a $C_3$–$C_{20}$ olefin and (d) repeating steps (a), (b), and (c) so as to achieve an overall higher yield of 2,6-dialkylphenol.

13. The process of claim 12 wherein said alkyls are tertiary.

14. The process of claim 12 wherein said olefin is isobutylene.

15. A cyclic process for the production of 2,6-dialkylphenols wherein the alkyl groups are sec- or tert-alkyl groups, said process comprising (a) reacting at about 100–1000 psig and 75°–250° C. a phenolic reactant comprising mainly phenol with a $C_3$–$C_{20}$ olefin in the presence of an aluminum phenoxide-type catalyst to form an alkylation mixture (b) distilling said 2,6-dialkylphenol from said alkylation mixture leaving distillation bottoms comprising a para-alkylphenol mixture comprising 2,4-dialkylphenols and 2,4,6-trialkylphenols and (c) recycling at least part of said bottoms to a subsequent cyclic process conducted in the same manner including the above steps (a) and (b) wherein, in said subsequent cyclic process said bottoms form about 20–30 weight percent of said phenolic reactant.

16. The process of claim 1 wherein said phenolic mixture comprising at least about 70 weight percent phenol also contains 2-alkylphenol.

17. The process of claim 12 wherein said phenol mixture also contains ortho-alkylphenol.

18. The cyclic process of claim 15 wherein said phenolic reactant also contains a 2-alkylphenol.

19. The cyclic process of claim 15 wherein said phenolic reactant also contains a para-alkylphenol.

* * * * *